US 6,563,577 B2

(12) United States Patent
Oomori et al.

(10) Patent No.: US 6,563,577 B2
(45) Date of Patent: May 13, 2003

(54) DEFECT TESTING APPARATUS AND DEFECT TESTING METHOD

(75) Inventors: Takeo Oomori, Hachioji (JP); Koichiro Komatsu, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/836,185

(22) Filed: Apr. 18, 2001

(65) Prior Publication Data

US 2002/0005946 A1 Jan. 17, 2002

(30) Foreign Application Priority Data

Apr. 21, 2000 (JP) ........................................ 2000-120450
May 24, 2000 (JP) ........................................ 2000-153461

(51) Int. Cl.⁷ ............................................. G01N 21/00
(52) U.S. Cl. ................. 356/237.2; 356/237.1; 356/237.4; 356/237.5
(58) Field of Search ........................... 356/237.1, 237.2, 356/237.3, 237.4, 237.5, 237.6, 418; 359/754, 763

(56) References Cited

U.S. PATENT DOCUMENTS

| | | | |
|---|---|---|---|
| 4,299,443 A | * 11/1981 | Minami et al. ........... 356/237.1 |
| 4,609,291 A | * 9/1986 | Takahashi .................. 356/418 |
| 5,808,814 A | * 9/1998 | Kudo ........................... 359/754 |
| 5,907,396 A | * 5/1999 | Komatsu et al. ......... 356/237.1 |
| 6,160,615 A | * 12/2000 | Matsui et al. ............. 356/237.4 |
| 6,222,624 B1 | * 4/2001 | Yonezawa ................. 356/237.1 |
| 6,333,992 B1 | * 12/2001 | Yamamura et al. ......... 382/149 |

FOREIGN PATENT DOCUMENTS

| JP | 02 236 108 | * 10/1990 |
| JP | 5-232032 | 9/1993 |
| JP | 5-232040 | 9/1993 |
| JP | 7-027709 | 1/1995 |
| JP | 8-075661 | 3/1996 |
| JP | 2000-294609 | 10/2000 |

* cited by examiner

*Primary Examiner*—Michael P. Stafira
*Assistant Examiner*—Sang H. Nguyen
(74) *Attorney, Agent, or Firm*—Miles & Stockbridge P.C.

(57) ABSTRACT

The present invention aims of preventing a diffracted light, in testing to detect a foreign substance or a flaw on a tested substrate having a repeated pattern, from entering the eye of the observer or a light receiving optical system to be hindrance to the defect test, by providing a defect testing apparatus which comprising: a light source; an illumination optical system for applying a light flux from the light source onto a tested substrate having a repeated pattern at a predetermined angle of incidence; a light receiving optical system for receiving a scattered light from the tested substrate; an image pick-up device for picking up an image formed by the light receiving optical system; a display device for displaying the image obtained by the image pick-up device; and a test stage for mounting the tested substrate thereon at the time of testing, wherein the tested substrate and the illumination optical system are arranged to be rotatable relatively to each other.

14 Claims, 14 Drawing Sheets

DEFECT TESTING APPARATUS AND DEFECT TESTING METHOD

This application claims the benefit of Japanese Applications Nos. 2000-120450 and 2000-153461 which are hereby incorporated by reference.

BACKGROUND OF THE INVENTION

1. Field of the Invention

The present invention relates to a defect testing apparatus for detecting a defect such as a foreign substance or a flaw on the surface of a substrate which may be produced in the course of manufacture of a semiconductor device, or the like, especially in the course of manufacture of a semiconductor wafer, a liquid crystal display panel, etc.

2. Related Background Art

In a conventional testing apparatus, a scattered light from the surface of a substrate to be tested is observed to detect an abnormality such as a foreign substance (e.g. dust) or a flaw. For instance, there is an apparatus which is disclosed in the Japanese Patent Laid-Open Application Nos. 5-232032 and 5-232040. According to the disclosed method therein, this apparatus is arranged such that a light from a light source is applied onto an object to be tested, such as a wafer, so as to visually detect the scattered light therefrom, thereby conducting a defect test.

Also, according to a method disclosed in the Japanese Patent Laid-Open Application Nos. 7-27709 and 8-75661, it is arranged that a light from the light source is applied onto a tested object such as a wafer, and the scattered light therefrom is fetched by a light receiving optical system to obtain a dark field image, thereby detecting a defect from this image by an image processing.

To be described more specifically, in the course of manufacturing a semiconductor wafer or a liquid crystal display substrate, presence of a foreign substance such as a dust is a hindrance to a processing for forming a correct circuit pattern, such as an etching or CVD (Chemical Vapor Deposition). Accordingly, it is generally conducted, on the stage of printing and developing a pattern on a resist typically by means of an exposure machine, to test to detect an abnormality or a foreign substance on the printed pattern. Such a conventional test of this type is conducted by applying a light flux from an illumination optical system onto an object to be tested to be visually observed by a testing personnel, as disclosed in the Japanese Patent Laid-Open Application No. 5-232032 described above. In this case, if the light is applied onto a fine circuit pattern in the course of detection of a foreign substance, a diffracted light is produced, which results in difficulty in discriminating the scattered light which is produced by the foreign substance from the diffracted light which is produced by the circuit pattern. Moreover, since a pattern abnormality is detected by using a diffracted light, a result of the test is easily affected by the degree of skill or of fatigue of the testing personnel so that the test standard is unstable. Accordingly, in the above Japanese Patent Laid-Open Application No. 7-27709, such a method is disclosed in which the illumination is optimized in detecting a foreign substance and in detecting a pattern abnormality with application of the technology of an image processing so as to attain a test free from an individual difference of the testing personnel. In this case, in order to detect a foreign substance on the surface of a tested object, an illumination light from the light source is introduced into a light guide fiber to form a linear secondary light source. Then, a light from the linear secondary light source is transmitted through a condensing lens so that a light flux in the direction of the surface on which the illumination light is incident is collimated to be substantially parallel light fluxes. Thereafter, the light is applied onto the entire surface of the wafer at an angle of incidence of substantially 90°. The scattered light from the foreign substance on the wafer is received by the light receiving optical system which is disposed above the wafer, whereby the foreign substance is detected.

However, in such a testing apparatus, if fine repeated patterns are present on the tested object, the diffracted light may enter the eye of the observer or the light receiving optical system to be hindrance to detection of a defect under a certain condition, which leaves the possibility that an abnormality such as a foreign substance of a flaw can not be detected.

Furthermore, the conventional apparatus described above is arranged such that in order to minimize an amount of light to enter the surface of the tested object so as to detect a scattered light from a foreign substance at a highest contrast, the illumination light illuminates the tested object at an angle of incidence of substantially 90°. For this reason, when the wavelength of the illumination light and the pattern pitch of the tested object are substantially equal to each other, the diffracted light advances in a direction substantially perpendicular to the surface of the tested object so as to enter the light receiving optical system. The amount of the diffracted light from the circuit pattern is far greater, compared with that of the scattered light from the foreign substance. For this reason, there arises a problem that the foreign substance can not be detected when the diffracted light is incident on the light receiving optical system of the surface testing apparatus. Particularly, in a case as disclosed in the Japanese Patent Laid-Open Application No. 7-27709, in which the illumination light is applied in the entire circumferential direction of the tested object, since the diffracted light inevitably enters the light receiving optical system, a test on a foreign substance can not be conducted.

SUMMARY OF THE INVENTION

The present invention was contrived taking such problems into consideration, and its object is to provide a testing apparatus and method with high reliability, which is arranged such that a diffracted light does not enter a light receiving optical system and capable of detecting a foreign substance, and the like, correctly at high speed and with high precision.

According to the present invention, there is provided a defect testing apparatus which comprises a light source, an illumination optical system for applying a light flux from the light source onto a substrate to be tested having repeated patterns at a predetermined angle of incidence, a light receiving optical system for receiving a scattered light from the tested substrate, an image pick-up device for picking up an image which is formed by the light receiving optical system, a display device for displaying the image obtained by the image pick-up device, and a test stage for mounting the tested substrate thereon at the time of testing, characterized in that the tested substrate and the illumination optical system are arranged to be rotatable relatively to each other.

The defect testing apparatus of the present invention may be arranged such that the test stage is rotatable around the axis in the normal direction of the tested substrate. Or, an alignment stage may be disposed separately to conduct alignment around the axis in the normal direction of the substrate prior to the test.

Moreover, the defect testing apparatus of the present invention preferably comprises a light receiving optical system which is telecentric on the side of the tested substrate.

Also, the defect testing apparatus of the present invention is preferably arranged, when a light is applied on the tested substrate with the spread angle on a flat surface which is perpendicular to the entrance surface of the illumination optical system and contains the optical axis, to rotate such that an angle of rotation between the optical axis of the illumination optical system and the direction of arrangement of lines of the repeated pattern is more than or equal to ½ of the spread angle.

Moreover, in the defect testing apparatus of the present invention, even when the repeated pattern has two or more directions of arrangement, the test stage or the alignment stage can be rotated to satisfy predetermined conditions.

Furthers the defect testing apparatus of the present invention may comprise light flux shaping member which makes the spread angle variable, or a calculation device for determining the spread angle and an angle of rotation of the tested substrate on the basis of pattern information of the tested substrate, or an image processing device for conducting an image processing to detect a defect on the basis of the information obtained by the image pick-up device. In this manner, it becomes possible to automatically conduct defect detection.

According to the present invention, the illumination optical system comprises not less than three groups of optical devices having a refracting power at least on a first plane containing the optical axis of the illumination optical system, and optical devices having a refracting power on a second plane which is perpendicular at least to the first plane and contains the optical axis. In this case, the term "the refracting power" contains the reciprocal of the focal length of a reflection system, in addition to the reciprocal of the focal length of a transmission (refraction) system, such as a lens or a refracting surface. In addition, the term "the optical devices" contains a transmission (refraction) optical device or a reflection type optical device.

In an actual circuit device or a liquid crystal display device, manufactured devices stand in line in an orderly manner so that directions in which diffracted lights are produced are limited. That is, if the tested object is rotated on the horizontal plane, the direction of the diffracted light is changed so that conditions for preventing the diffracted light from entering the light receiving optical system can be selected. According to the structure of the present invention described above, a range for the angle of incidence of the light flux for illuminating the tested object can be limited to a narrow one, so that it is possible to easily find the conditions which prevent a comparative alignment of the direction of incidence of the light flux for illuminating the surface of the tested object with the direction of repetition of patterns formed on the tested object, that is, the conditions for an azimuthal direction for preventing the diffracted light from entering the light receiving optical system.

It is also necessary to satisfy such conditions as preventing the diffracted light coming from the surface of the tested object from entering any part on the entire surface of the tested object, as described above, in order to convert images produced by a scattered light from the surface of the tested object into image signals collectively by means of an image pick-up device. To this end, according to the present invention, any point on the tested object is illuminated under the uniform illuminating conditions by employing a so-called telecentric illumination method in which light fluxes for illuminating respective points on the tested object are made to be substantially parallel to each other by means of the above-described arrangement.

As a preferable embodiment of the invention, the light receiving optical system preferably comprises an image pick-up device unit and preferably comprises a wavelength selection device for selecting a light with a specific wavelength on the illumination optical system side rather than the image pick-up device unit side.

If the wavelength of the illumination light is different, an angle of diffraction from a pattern is different. As a result, it is possible to prevent the diffracted light from entering the image pick-up device unit of the light receiving optical system by selecting or limiting the wavelength of the illumination light. In other words, even when a diffracted light enters the light receiving optical system with the specific wavelength of A nm, it is possible to prevent the diffracted light from entering the image pick-up device unit of the light receiving optical system with another wavelength of B nm. According to the present invention, in addition to the structure which allows a relative rotation between the tested substrate and the illumination optical system, there is provided a wavelength selection device so as to prevent a diffracted light from entering the image pick-up device unit more effectively. It is desirable to dispose a member for selecting the wavelength of a light to be received, such as a filter, between the light source unit for supplying the illumination light and the image pick-up device.

DESCRIPTION OF THE PREFERRED EMBODIMENTS

First Embodiment

Figure 1:
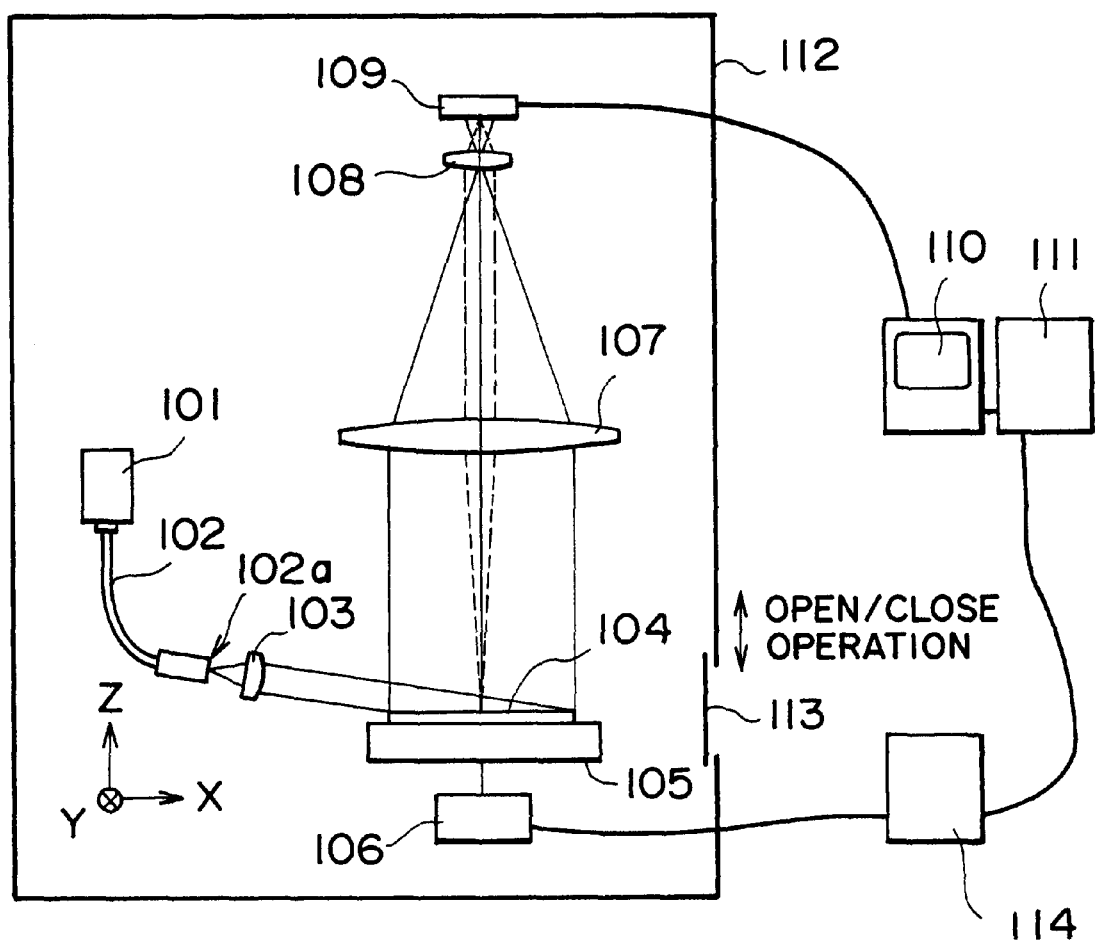
FIG. 1 is a view for showing the entire structure of a defect testing apparatus according to a first embodiment of the present invention.

FIG. 1 is a view for showing the entire structure of a defect testing apparatus according to the first embodiment of the invention. In FIG. 1, the entrance surface for an illumination light flux is on the sheet surface, i.e., the X-Z plane.

Referring to FIG. 1, a lamp house 101 contains a light source, such as a halogen lamp or a metal halide lamp, and is provided with a lens and an exchangeable wavelength selecting filter, so as to use only a light having a specific wavelength. A light from the lamp house 101 is passed through a light guide 102 to illuminate a wafer 104 at an angle of incidence of 85° to 90°. The end surface of the light guide on its exit side is in the form of a slit which is long in a direction perpendicular to the sheet surface (Y direction) and is short in the direction perpendicular to this longitudinal direction. The slit-like light flux is collimated by a cylindrical lens 103 on the surface in the latitudinal direction of the slit, whereby the light emitted from the end surface 102a of the light guide 102 illuminates the entire surface of the wafer with efficiency. Since the angle of incidence is large to be 85° to 90°, the length of the cylindrical lens 103 in the latitudinal direction can be reduced.

The wafer 104 is mounted onto a test stage 105 from outside a chamber 112 through an open/close window 113 by means of an unrepresented conveying (carrying) device, such as a robot arm. The test stage 105 is rotatable by means of a driving mechanism 106, or the like, and an alignment in the direction of rotation is conducted. After the wafer 104 is mounted, the open/close window 113 is closed, whereby any stray light which may come from outside the apparatus can be shielded. Thus, a test with efficiency and high reliability can be conducted.

When the wafer 104 has a defect such as a foreign substance or a flaw, a scattered light is produced. The scattered light is received by a light receiving lens 107 of a light receiving optical system. The optical axis of the light receiving lens 7 is parallel to the normal line of the wafer 104. Since the entrance pupil of an imaging lens 108 is disposed substantially at the same position as the focal length of the light receiving lens 107, the object side thereof is formed to be a telecentric optical system. For this reason, only the lights scattered substantially in the direction of the normal line of the wafer 104 are condensed, and the image of the foreign substance or the flaw produced by the scattered lights is formed by an image pick-up device 109 through the imaging lens 108. The image pick-up device 109 comprises, for instance, a CCD. Note that a reflection mirror can be used, instead of the light receiving lens 107.

The display device 110 typically comprises a CRT or a liquid crystal panel display, and displays the pick-up image of a defect such as a foreign substance or a flaw. An image processing device 111 processes an image which is fetched by the image peck-up device 109, and transmits information on the position or the size of the defect to the display device 110. The display device 110 can display such defect information, also.

The image processing device 111 detects the position of an orientation flat or a notch of the wafer 104 with a light scattered by the outer periphery of the wafer 104, and transmits this information to a calculation device 114. The calculation device 114 calculates a suitable angle of rotation for a test on the basis of the transmitted position of the orientation flat or the notch and transmits this positional information to the driving device 106.

The driving device 106 rotates the test stage 105 on the basis of this positional information, and conducts alignment of the wafer 104 at a predetermined angle. The alignment based on image processing may take time sometimes. In such cases, an unrepresented special stage (alignment stage) is separately provided, and the wafer may be mounted on the test stage 105 after the alignment is completed by a method other than the image processing.

It was described above that only the lights scattered substantially in the direction of the normal line of the wafer 104 are received by the light receiving optical system. However, a fine repeated pattern is formed on the wafer 104 to produce a diffracted light, which may enter the light receiving optical system as a stray light. In case of a repeated pattern in one direction, the diffracted light enters the light receiving optical system when the following general expression of a diffraction condition is satisfied:

$$\sin \theta d - \sin \theta i = m\lambda/P,$$

where $\theta d$ is an angle of diffraction from the wafer, and $\theta i$ is an angle of incidence onto the wafer. From this general expression, in the apparatus shown in FIG. 1, the angle of incidence is great to be 85° to 90°, so that a light in the direction of the normal line of the wafer is received. Then, when the direction of illumination is the same as the direction of arrangement of the repeated pattern and if the pitch p of the repeated pattern is substantially m time (m is an integer) as larger as the wavelength $\lambda$ of the illumination light, a diffracted light of m-th order or −m-th order enters the light receiving optical system.

Figure 2A:
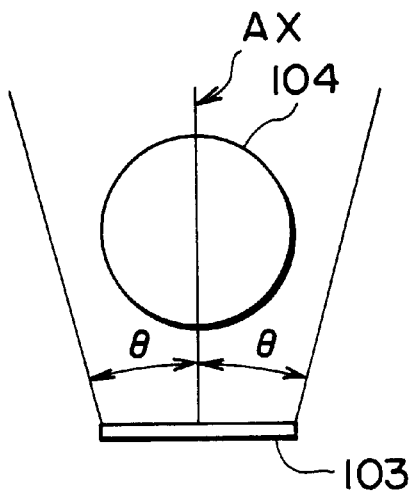
FIGS. 2A and 2B are plane views for explaining a relationship between an illumination light flux and a wafer or repeated patterns.
Figure 2B:
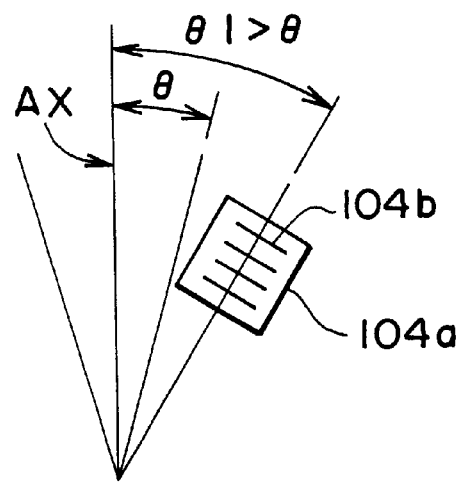

In order to prevent the entrance of the diffracted light, the wafer 104 is rotated around the normal line thereof at the time of alignment. FIGS. 2A and 2B are plane views for explaining the directional relationship between the illumination light flux and the wafer or the repeated pattern, in which FIG. 2A is a top view of the wafer 104 and the cylindrical lens 103 of FIG. 1, seen from the light receiving lens 107 side, and FIG. 2B is a view for showing an extracted part of the pattern which is formed on the wafer 104 in this top view.

To be stated strictly, the spread angle of 2θ is an angle by which the light flux spreads on the surface which is perpendicular to the entrance surface and contains the optical axis. In the following description, for simplicity, the angle by which the illumination light flux spreads on the sheet surface, that is, on the flat plane containing the surface of the wafer 104 is referred to as the spread angle 2θ, in FIGS. 2A and 2B. This approximation is established substantially completely if the angle of incidence of the illumination light flux onto the wafer 104 is large. As shown in FIG. 2B, when the wafer 104 is rotated in such a manner that the angle θ1 between the optical axis of the illumination light flux (approximately, the optical axis AX projected on the sheet surface) and the direction of arrangement of lines 104b (the direction perpendicular to the lines 104b) is greater than the angle θ, the direction of arrangement of repeated patterns 104a becomes greater than a half θ of the spread angle. Thus, the direction of the diffracted light deviates from the direction of the normal line of the wafer 104 so that only the scattered light can be received.

Figure 3A:
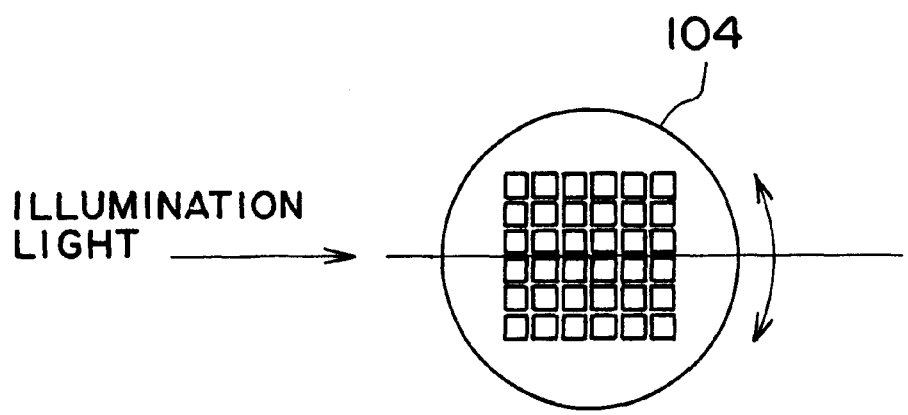
FIGS. 3A and 3B are plane views for showing two kinds of repeated patterns respectively having two directions existing on a wafer.
Figure 3B:
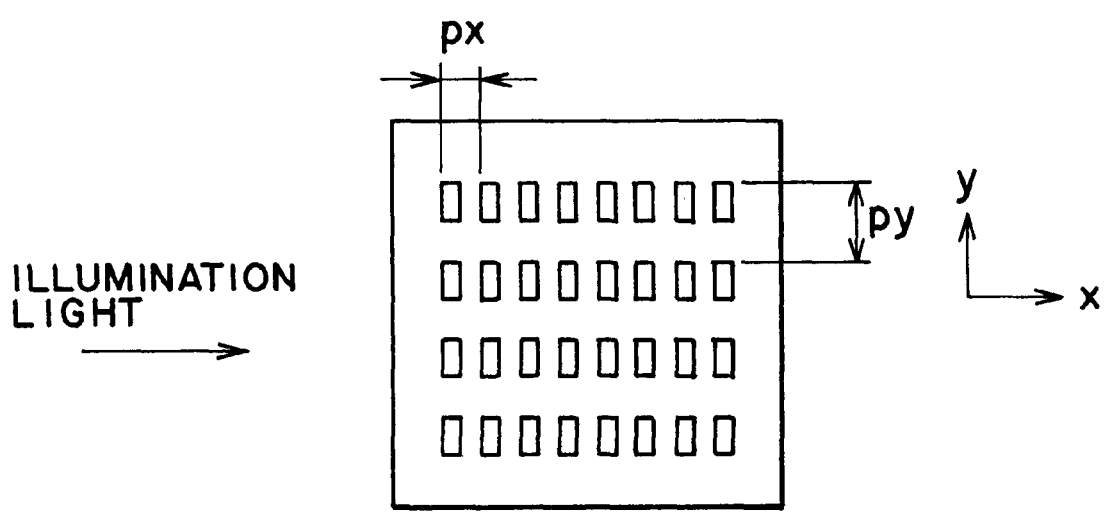

When the repeated patterns are disposed in two directions, unlike in case of one direction, the diffracted light may enter the light receiving optical system even if the wafer 104 is rotated. FIGS. 3A and 3B are plane views for showing two kinds of repeated patterns on the wafer which respectively have two directions, in which FIG. 3A is a plane view for showing a state of arrangement of chips on the entire surface of the wafer, and FIG. 3B is a plane view for showing a state of arrangement of patterns on one chip.

In the apparatus shown in FIG. 1, the conditions for advancing the diffracted light in the direction of the normal line of the wafer 104 are as follows:

$$\tan\theta 1 = mypx/mxpy \quad (1);$$

$$-px/\lambda \leq mx \leq 0 \quad (2);$$

$$-py/\lambda \leq my \leq 0 \quad (3);$$

and $$(mx\lambda/px)^2 + (my\lambda/py)^2 = 1 \quad (4),$$

where θ1 is an angle of rotation of the wafer 104, px and py are pattern pitches in the X direction and the Y direction, respectively, mx and my are diffraction orders in the X direction and the Y direction, respectively, and λ is the wavelength of the illumination light. As shown in FIGS. 3A and 3B, the direction of incidence of the illumination light is perpendicular to the Y direction, and in parallel to the X direction. Since the range for the angle θ1 is from 0° to 90°, the direction of rotation thereof may be either clockwise or anti-clockwise in FIGS. 2A to 3B.

Since the illumination light flux has a spread of ±θ, it can be well considered the angle θ1 has the spread of ±θ. Then, in case of the repeated patterns in two directions, the wafer 104 is rotated by selecting such an angle of rotation as deviating from the range θ1±θ at the time of alignment. For instance, assuming that the wavelength of the light source is 500 nm to 700 nm, px is 1 μm, and py is 2 μm, in accordance with the conditions (1) to (4), the diffracted light enters the light receiving optical system only when the order of the diffracted light, the angle of rotation of the wafer, and the wavelength are in any of the following combinations shown in Table 1.

TABLE 1

| Order (mx, my) | Angle of rotation (θ1) | Wavelength (λ) |
|---|---|---|
| −2, 0 | 0° | 500 nm |
| −1, −3 | 56° | 555 nm |
| 0, −4 | 90° | 500 nm |
| 0, −3 | 90° | 667 nm |

As seen from Table 1, the range of the angle at which the diffracted light enters is obtained by adding the spread of the illumination light to 0°, 56°, 90° serving as references, respectively. If the spread angle is ±15°, the range of the angle of rotation at which the diffracted light enters is from 15° to 41°, from 41° to 71°, or from 75° to 90°. Accordingly, it is possible, by rotating the wafer 104 in a range from 15° to 41° or from 71° to 75°, to receive scattered light only since the direction of the diffracted light deviates from the normal line of the wafer 104.

Information on the direction or the pitch of the repeated patterns with respect to the orientation flat or the notch, the spread angle of the illumination light flux, the wavelength, and so on, are supplied to the calculation device 114 in advance so that an appropriate angle of rotation is calculated. Further, since the object side is a telecentric optical system, diffraction conditions for the entering diffracted light are the same at any position on the wafer, which makes a calculation by the calculation device 114 easier. In case of a non-telecentric optical system having a different diffraction condition, the diffracted light may enter some areas on the wafer, and a calculation taking this probability into consideration is required.

Figure 14:
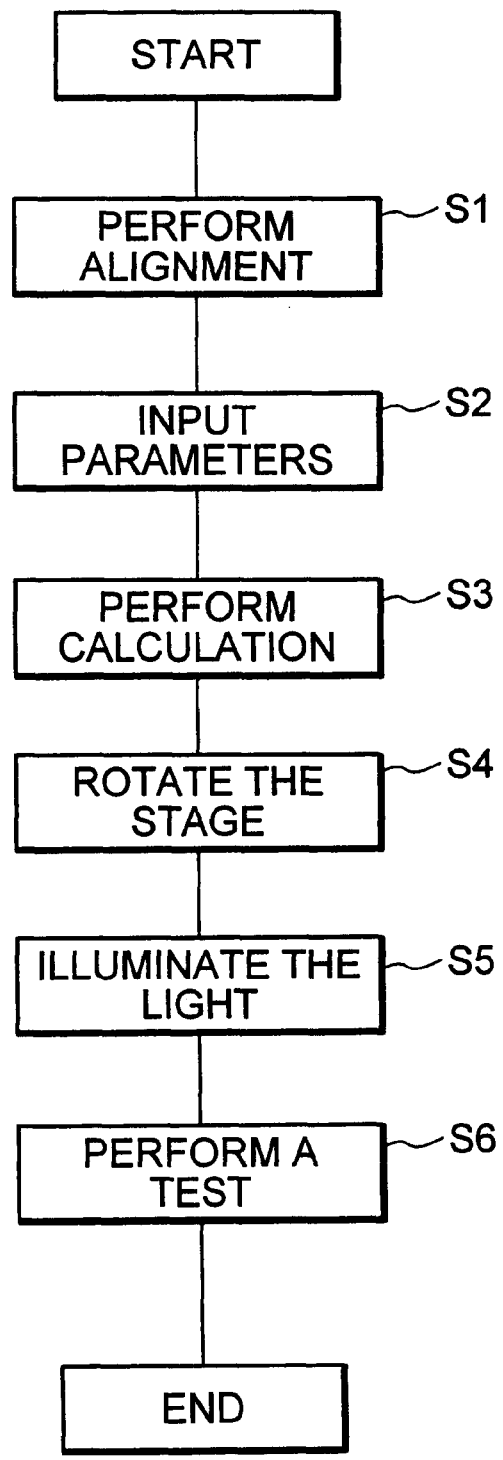
FIG. 14 is a flow chart for explaining a testing procedure according to the first embodiment.

FIG. 14 is a flow chart for showing a procedure of a defect test. In step S1, an unrepresented alignment device performs alignment of the wafer 104. In step S2, the operator supplies known parameters (the direction and the pitch of the repeated pattern, the spread angle, wavelength, and the angle of incidence of the illumination light flux, etc.) to the calculation device 114 through an unrepresented input device such as a keyboard, or the like. In step S3, the calculation device 114 calculates an appropriate angle of rotation. In step S4, the driving mechanism 106 rotates the test stage 105 only by the appropriate angle. In step S5, the illumination optical system illuminates the wafer 104. In step S6, a defect test is performed on the basis of a scattered light from the wafer 104.

When the parameters are to be input, if there is an unknown parameter, an amount of the angle by which the test stage 105 is rotated can not be calculated. In this case, it is desirable to determine an amount of the angle of rotation of the stage in advance and rotating the test stage 105 only by this amount, thereby performing the test.

Figure 15A:
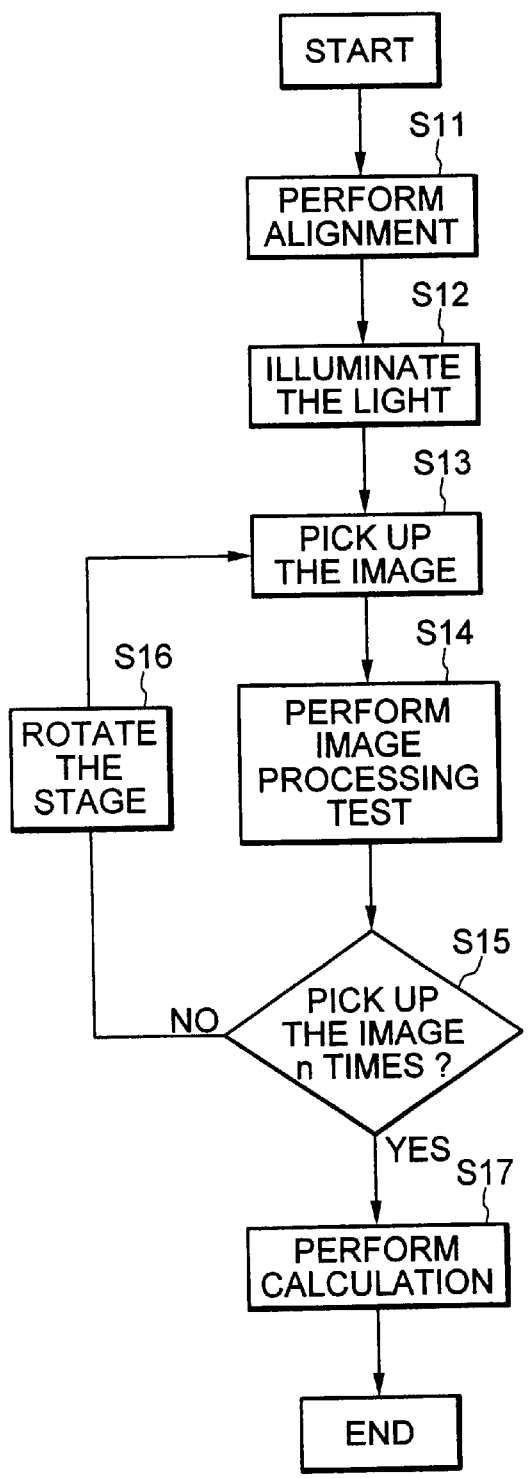
FIGS. 15A and 15B are flow charts for explaining other procedures according to the first embodiment.

Another procedure for the defect test with an unknown parameter will be described below with reference to FIGS. 15A and 15B.

First, the procedure shown in FIG. 15A will be described. In step S11, an unrepresented alignment device performs alignment of the wafer 104. In step 512, the illumination optical system illuminates the wafer 104. In step S13, the image of the wafer which is produced by a scattered light from the wafer 104 is picked up. In step S14, the defect test is performed on the picked-up image of the scattered light. In step S15, it is determined if the image is picked up n times. If no, the flow advances to step S16. In step S16, the test stage 105 is rotated only by a predetermined angle. In this state, the operations from step S13 to step S15 are repeated. If it is determined that the image is picked up n times in step S15, the flow advances to step S17. In step S17, a test result of the n images is further image-processed, thereby performing a final defect test.

For example, the wafer 104 is illuminated in a state where the light from the illumination optical system is incident at 45 degree to a predetermined line on the wafer 104. A first image pick-up is conducted in this state. Next, if n=4, stage 105 is rotated at every angle of 360/4=90 degree, and the image pick-up is conducted 3(=n−1) times. Namely, stage 105 is rotated at an angle of 90, 180, 270 degree, and the image pick-up is conducted at the every angle. Finally, the above-mentioned procedures are conducted on the basis of the 4 data.

Next, the procedure shown in FIG. 15B will be described. In step S21, the unrepresented alignment device performs alignment of the wafer 104. In step S22, the illumination optical system illuminates the wafer 104. In step S23, the image of the wafer which is produced by a scattered light from the wafer 104 is picked up. In step S24, it is determined if the image is picked up n times. If no, the flow advances to step S25. In step S25, the test stage 105 is rotated only by the predetermined angle. In this state, the operations from step S23 to step S24 are repeated. If it is determined that the image is picked up n times in step S24, the flow advances to step S26. In step S26, the n images are synthesized by an image processing and a defect test is performed on the synthesized image.

Figure 15B:
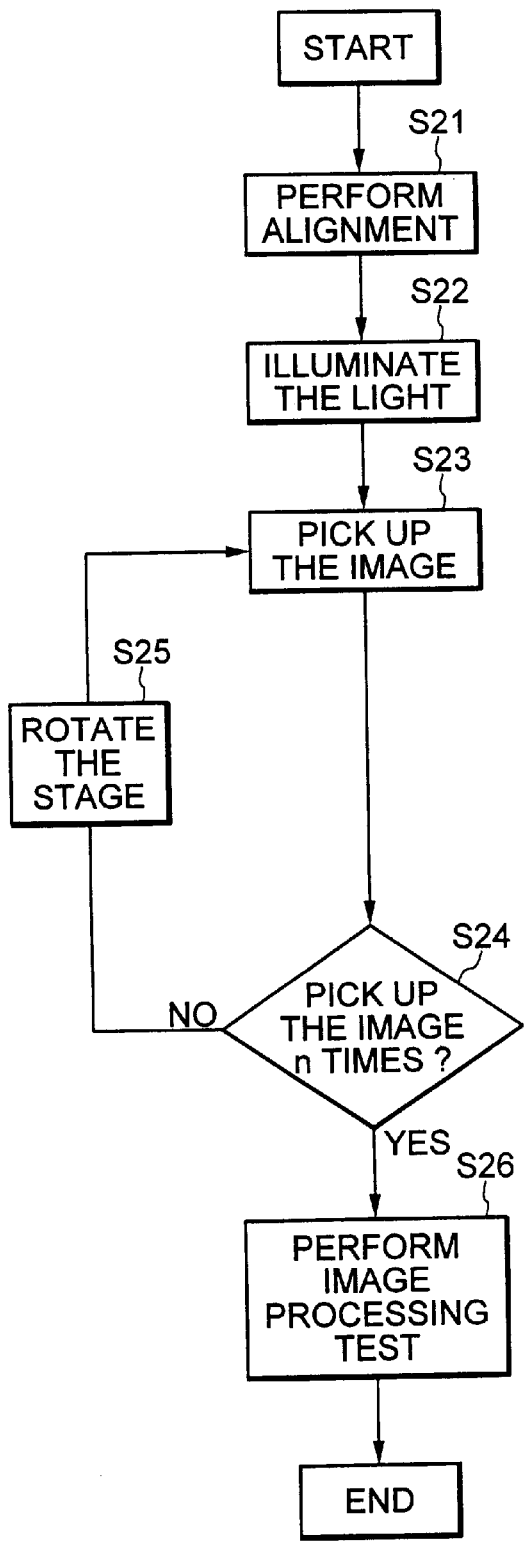

For example, in the similar way, if n=4, the procedures shown in FIG. 15B are conducted on the basis of 4 data obtained at a time when the stage 105 is located at the predetermined direction, 90, 180, 270 degree.

Since areas in which the diffracted light is produced on the wafer 104 are disposed at regular intervals, if the information on the direction or the pitch of the repeated pattern, the spread angle and wavelength of the illumination light flux, etc., have not been supplied to the calculation device 114, the wafer 104 is continued to rotate until the diffracted light ceases to enter. Whether the diffracted light enters or not is judged by the image processing device 111. When no light is received at regular intervals, it is judged that the diffracted light ceased to enter. The angle of rotation θ1 for one wafer is not limited to one value. Plural values, i.e., variations of the angle θ1 are subjected to the test under plural conditions. If a defect is detected under one of the conditions, it can be determined that the wafer 114 is defective. If any flaw is present on the wafer, the intensity of the scattered light from the flaw changes depending on a direction of illumination, so that the test with plural values is specially effective in case of a flaw.

The above descriptions assume an automatic test by the image processing device 111 as a precondition. However, there arises no problem if an image displayed on the display device 110 is visually tested without using the image processing device 111.

Repeated patterns existing on the same chip are of various kinds, depending on a production process of the semiconductor, and directions thereof are not the same. As a result, even if the angle of rotation is appropriate with one pattern, it may be inappropriate with another so that a diffracted light may be mixed.

Figure 4:
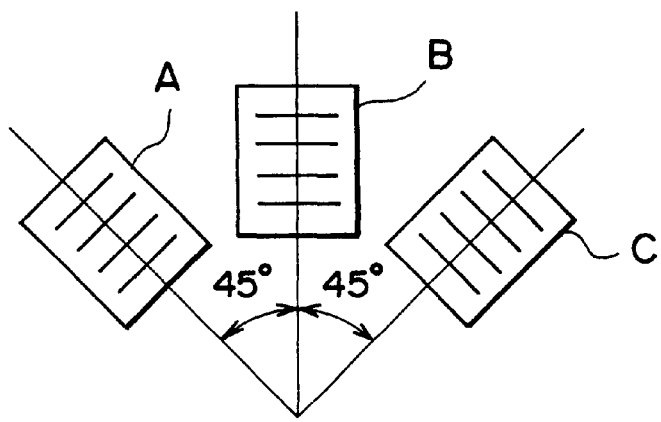
FIG. 4 is a plane view for showing a state of arrangement of three kinds of repeated patterns A, B and C.

Assuming, for instance, that there are three kinds of repeated patterns, and for a direction of arrangement of one specific pattern, there are another two patterns which make ±45° with the above pattern, respectively. FIG. 4 is a plane view for showing a state of arrangement of three kinds of repeated patterns A, B and C. Each of the patterns A and C makes 45° with the direction of arrangement of the pattern B. When the spread angle 2 θ of the illumination light flux is 60°, it is preferable to rotate the adjacent two patterns by 30° or more. In this case, however, though mixture of the diffracted light can be prevented with respect to these two patterns, the mixture thereof with respect to the remaining pattern can not be prevented, because the spread angle of the illumination light is great to be 60°.

As a result, it is desirable to set the spread angle of the illumination light to be small. To this end, it is desirable to use a light guide fiber having a small aperture angle or to set a small value for the numerical aperture for making the light incident onto the light guide 102 inside the lamp house, which results in a small numerical aperture of the illumination light emitted from the light guide 102.

Furthermore, if the wavelength range of the illumination light is set to be narrow, the effect of preventing the entry of the diffracted light is more satisfactory. For instance, in case of the two-directional patterns described above, there are four combinations of conditions for mixing the diffracted light, as shown in Table 1. In this case, if the wavelength is reduced from a range from 500 nm to 700 nm to a range from 600 nm to 700 nm, one combination remains as seen from Table 1. Then, the degree of mixture is reduced proportionally. If the wavelength width of the light is reduced to a several nm by means of an interference filter, or the like, it is possible to eliminate such a mixture itself. This arrangement for reducing the wavelength width will be described later.

If the numerical aperture and the half width of the wavelength are reduced too much, an amount of illumination decreases and the intensity of the scattered light is lowered. Thus, it is desirable that the numerical aperture and the wavelength width should be selected so long as not to be hindrance to the test.

Figure 5:
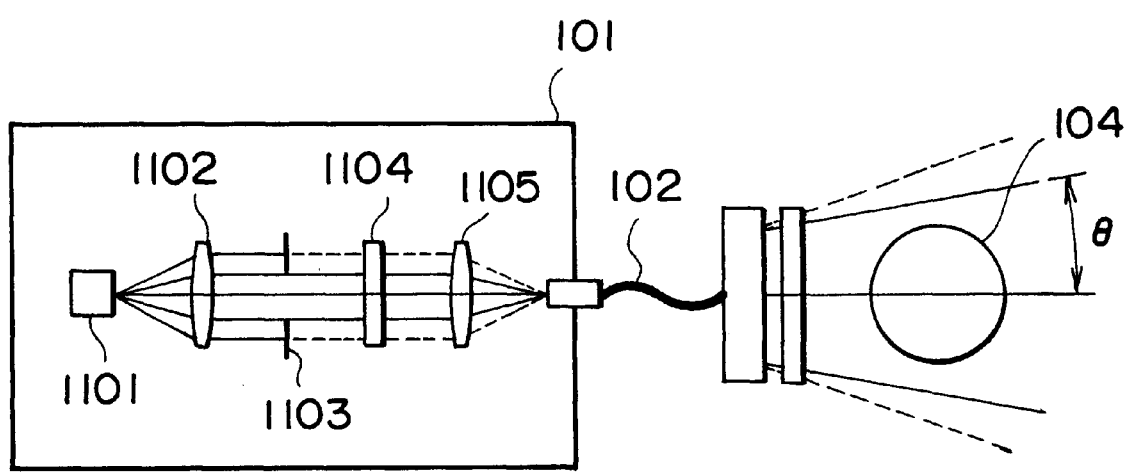
FIG. 5 is a partial structural view for showing a lamp house and an illumination optical system of a defect testing apparatus according to the first embodiment of the present invention.

FIG. 5 shows a structure of a lamp house capable of changing the numerical aperture to an arbitrary value. Referring to FIG. 5, a light emitted from a light source 1101 is collimated by a lens 1102 to be light fluxes substantially parallel to each other. A variable aperture stop 1103 changes the diameter of the light flux by changing the size of the aperture. In FIG. 5, the dotted line indicates the light flux when the variable aperture stop 1103 is opened, while the solid line indicates the light flux when the variable aperture stop 1103 is closed. An interference filter 1104 selectively fetches a light having the half width of several nm to several ten nm with respect to the reference wavelength. It is also possible to prepare a plurality of other interference filters (not shown) and to arrange them to be replaceable with each other time to time.

The illumination light flux passed through the interference filter 1104 is condensed by a lens 1105 and enters the light guide 102. In this case, the numerical aperture of the light entering the light guide 102 changes in accordance with the diameter of the variable aperture stop 1103, as indicated by the dotted line and the solid line. The changed numerical aperture becomes the numerical aperture of the emitted light as it is, which means that, in FIG. 5, the spread angle 2θ is changed. In this case, it is possible to conduct the test by determining the diameter of the interference filter 1104 and that of the variable aperture stop 1103 in accordance with the information from the calculation device 114.

Instead of rotating the wafer 104, the illumination optical system may be rotated.

Also according to the present invention, the structure of the optical system in the longitudinal direction and the latitudinal direction of an illumination light flux for illuminating a tested object, by the use of an optical device which is not to be rotated with respect to the optical axis of a cylindrical lens, or the like. In order to illuminate the longitudinal direction of the illumination light flux, it is required to make a light flux from the light source or the secondary light source to be substantially equal to the length of the illumination light flux in the longitudinal direction. As a result, a comparatively long focal length is required for a so-called condenser lens or a condenser mirror. On the other hand, in the latitudinal direction of the illumination light flux, a long focal length is not required for the condenser lens or the condenser mirror. Rather, a short focal length is preferable, in order to apply a light flux from the light source onto the tested object. Accordingly, a relay optical system in the latitudinal direction is constituted by a cylindrical lens or a cylindrical mirror which has no refracting power in the longitudinal direction of illumination. Then, the light source or the secondary light source is disposed to be in the vicinity of a pupil plane or a pupil conjugate plane of the illumination optical system both in the longitudinal direction and in the latitudinal direction of the illumination light flux. With this arrangement, it is possible to arrange such that the center of a light flux for illuminating any point on the tested object such as a wafer has a predetermined angle of incidence and an angle at which the illumination light flux is incident is within a predetermined range. Moreover, a mechanism for switching wavelengths of the light is arranged to detachably attach a color glass filter or an interference filter to the illumination optical system or the light receiving optical system. With this arrangement, the wavelength of a light to be received may be limited, or a device having diffusion such as a diffraction grating may be provided in the light source unit for conducting illumination with a predetermined wavelength.

Second Embodiment

Figure 6:
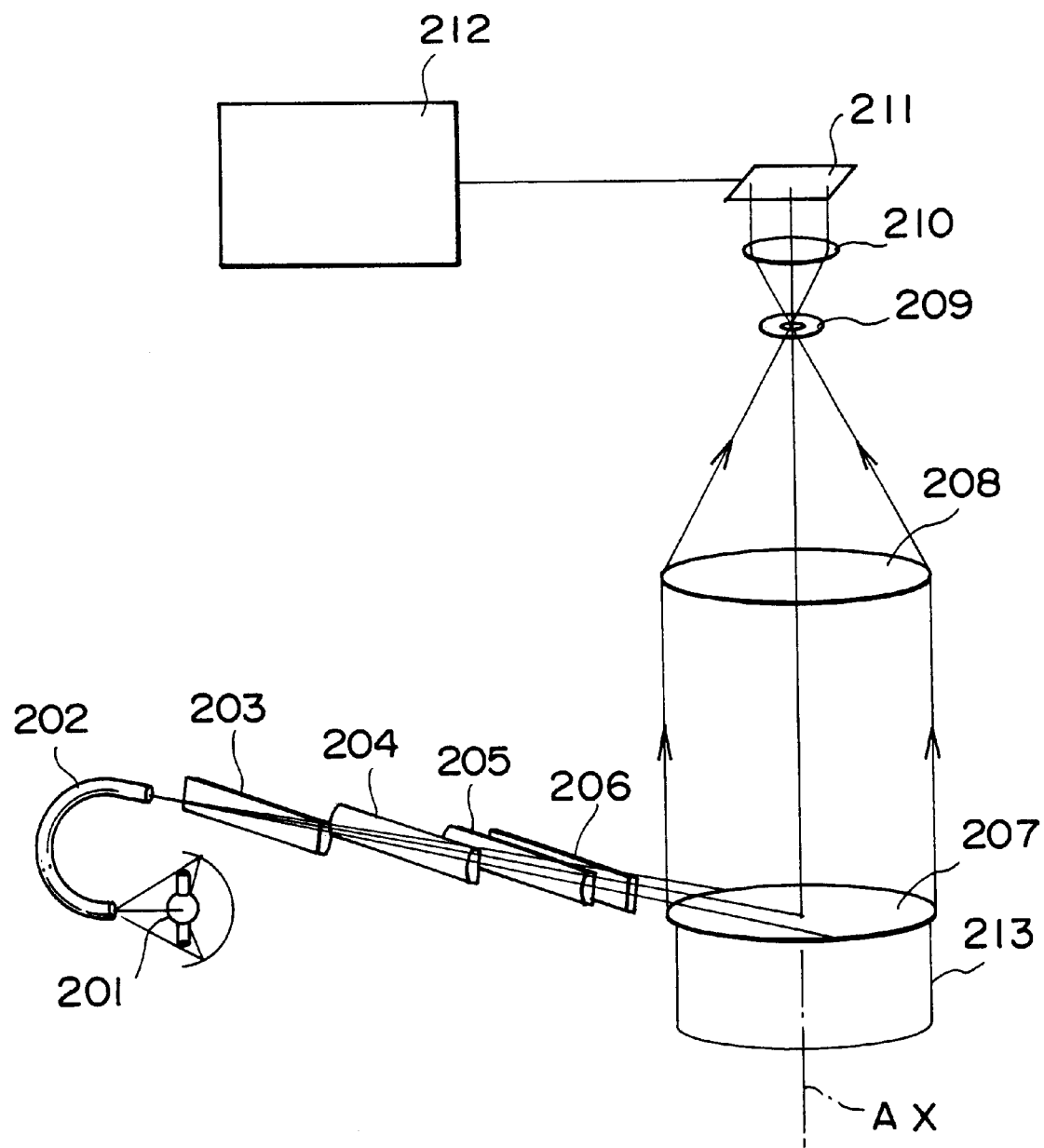
FIG. 6 is a view for showing the structure of a defect testing apparatus according to a second embodiment of the present invention.
Figure 7A:
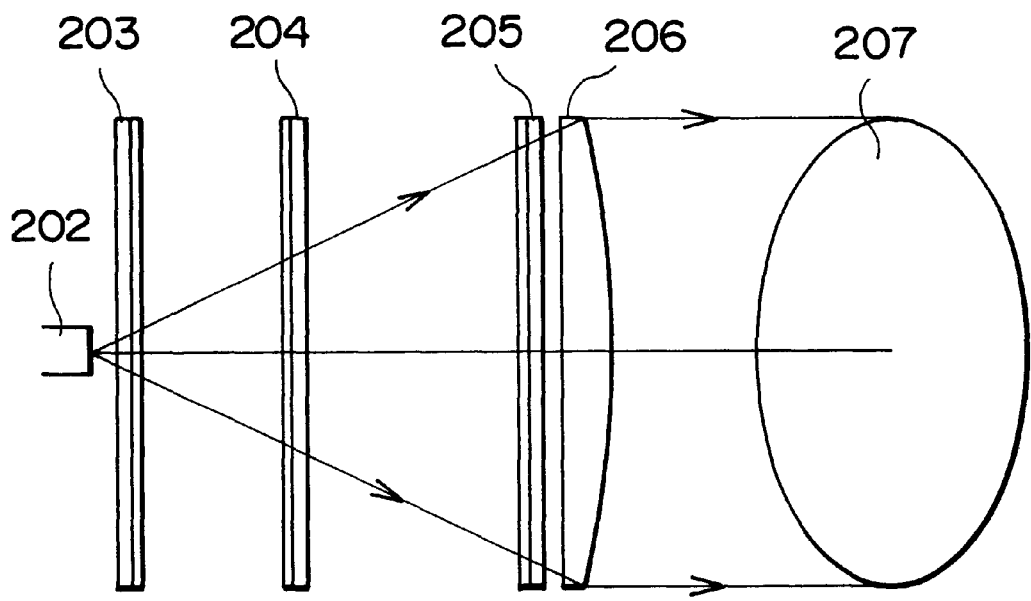
FIGS. 7A and 7B are views for showing the lens structures of an illumination optical system of the defect testing apparatus according to the second embodiment.
Figure 7B:
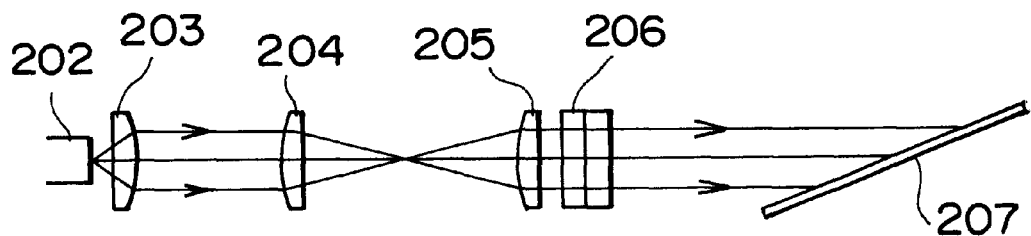

FIG. 6 is a view for showing the structure of a defect testing apparatus according to the second embodiment. Referring to FIG. 6, lights from an incandescent lamp, such as a halogen lamp, or a discharge light source 201, such as a mercury lamp or a metal halide lamp are condensed to be introduced into a light guide fiber 202. This light guide fiber 202 is comprised of optical fibers randomly collected in a bundle, and an exit end thereof serves as a secondary light source with a comparatively uniform luminous intensity. An illumination light emitted from the exit end of the fiber 202 illuminates a tested object 207 such as a wafer or a liquid crystal substrate at a predetermined angle through a first cylindrical lens 203, a second cylindrical lens 204, a third cylindrical lens 205, and a fourth cylindrical lens 206 which has a refracting power in a direction perpendicular to the above first to third cylindrical lenses 203, 204 and 205. In this case, the first to third cylindrical lenses 203 to 205 are disposed to have a refracting power on the surface onto which the illumination light flux is incident in a slanting manner. On the other hand, the fourth cylindrical lens 206 has a refracting power on a surface perpendicular to the surface on which the illumination light flux is incident in the slanting manner, and is disposed to illuminate the entire surface of the tested object 207. FIG. 7A is a top view of this illumination optical system, and FIG. 7B is a side view thereof. Returning to FIG. 6, the tested object 207 is mounted on a holder 213 which has the normal line on its surface rotatable around the axis AX. Then, a foreign substance or a flaw attached on the surface of the tested object 207 scatters the illumination light. A part of the scattered light is condensed by a light receiving optical system 208 which is disposed above substantially perpendicularly to the tested object 207, so as to form an image from the scattered light of the tested object 207 on an image pick-up device 211 through an aperture stop 209 and an imaging optical system 210. The image pick-up device 211 photoelectrically converts the scattered light to obtain a foreign substance signal. A signal processing system 212 judges whether there is a foreign substance on the tested object 207 or not.

When the tested object 207 takes a circular form having the radius R, like a semiconductor wafer, the illumination light flux takes an elliptical form having the diameter 2R in the longitudinal direction and the diameter 2R cos θa in the latitudinal direction, when the angle of incidence of the illumination light is θa. For instance, in order to illuminate a semiconductor wafer having the diameter of 200 mmØ at the angle of incidence of 85°, the light flux takes an elliptic form of 200 mm in the longitudinal direction and about 17.4 mm in the latitudinal direction. When the angle of incidence is great, like in this case, the light flux takes a very flat elliptic form. In order to illuminate the object in such a manner that the illumination light flux is incident at any point of such a flat elliptic form at a angle in a predetermined range, the light source or the secondary light source is required to be disposed in the vicinity of the front focal position of a condenser lens. However, in case of an ordinary condenser lens which is formed to be rotation-symmetrical, when the condenser lens illuminates a flat illumination area as described above, the light is applied also onto a part outside the illumination area so that the illumination is conducted with poor efficiency.

Accordingly, it is arranged such that a light flux in the latitudinal direction is relayed by the use of the cylindrical lenses 203 to 205 so that the exit end of the fiber 202 serving as the secondary light source is aligned with the synthesized front focal position of the relay optical system. In this case, it is required to satisfy the following expression:

$$\frac{1}{F}\left(e_3 + e_2 - \frac{e_3 e_2}{f_3}\right) = 1 - \frac{e_1}{f_1}$$

$$F\left(1 - \frac{e_2}{f_3}\right) = e_1 + e_0 - \frac{e_1 e_0}{f_1}$$

$$F\left(\frac{1}{f_2} + \frac{1}{f_3} - \frac{e_2}{f_2 f_3}\right) = 1 - \frac{e_0}{f_1}$$

where the focal lengths of the cylindrical lenses 203 to 205 are respectively $f_1$, $f_2$ and $f_3$, the distance between the light source and the principal plane of the cylindrical lens 203 is $e_0$, the distance between the principal plane of the cylindrical lens 203 and that of the cylindrical lens 204 is $e_1$, the distance between the principal plane of the cylindrical lens 204 and that of the cylindrical lens 205 is $e_2$, the distance between the principal plane of the cylindrical lens 205 and the center of the tested object 207 is $e_3$, and the synthesized focal length of the cylindrical lenses 203 to 205 is F.

Furthermore, since having the refracting power in the longitudinal direction of the illumination light flux, the fourth cylindrical lens 206 requires a comparatively long focal length. In this case, if the focal length of this lens is $f_0$, it is preferable that the distance between the exit end of the fiber 202 and the principal plane of the fourth cylindrical lens 206 is equal to $f_0$, and the distance between the principal plane of the fourth cylindrical lens 206 and the center of the tested object 207 is also equal to $f_0$. For this reason, the distance between the exit end of the fiber 202 and the tested object 207 is substantially equal to $2f_0$. That is, it is further required to satisfy the following expression for the optical systems 203 to 205 in the latitudinal direction:

$$2f_0 = e_1 + e_2 + e_3.$$

Moreover, since the tested object 207 is to be illuminated in a slanting manner, the operational distances between the center of the tested object 207 and the optical systems 203 to 206 are required to be sufficiently large. Values for these distances will be shown in Table 2. Provided that the composite focal lengths F takes a negative value with a reversed sign since the light is condensed after the light source image is once formed and then reversed.

TABLE 2

| $e_0$ | 18 mm | $f_1$ | 18 mm |
|---|---|---|---|
| $e_1$ | 3.6 mm | $f_2$ | 72 mm |
| $e_2$ | 192 mm | $f_3$ | 120 mm |
| $e_3$ | 360 mm | F | −30 mm |
| Total length | 573.6 mm | $f_0$ | 286.8 mm |

Figure 8:
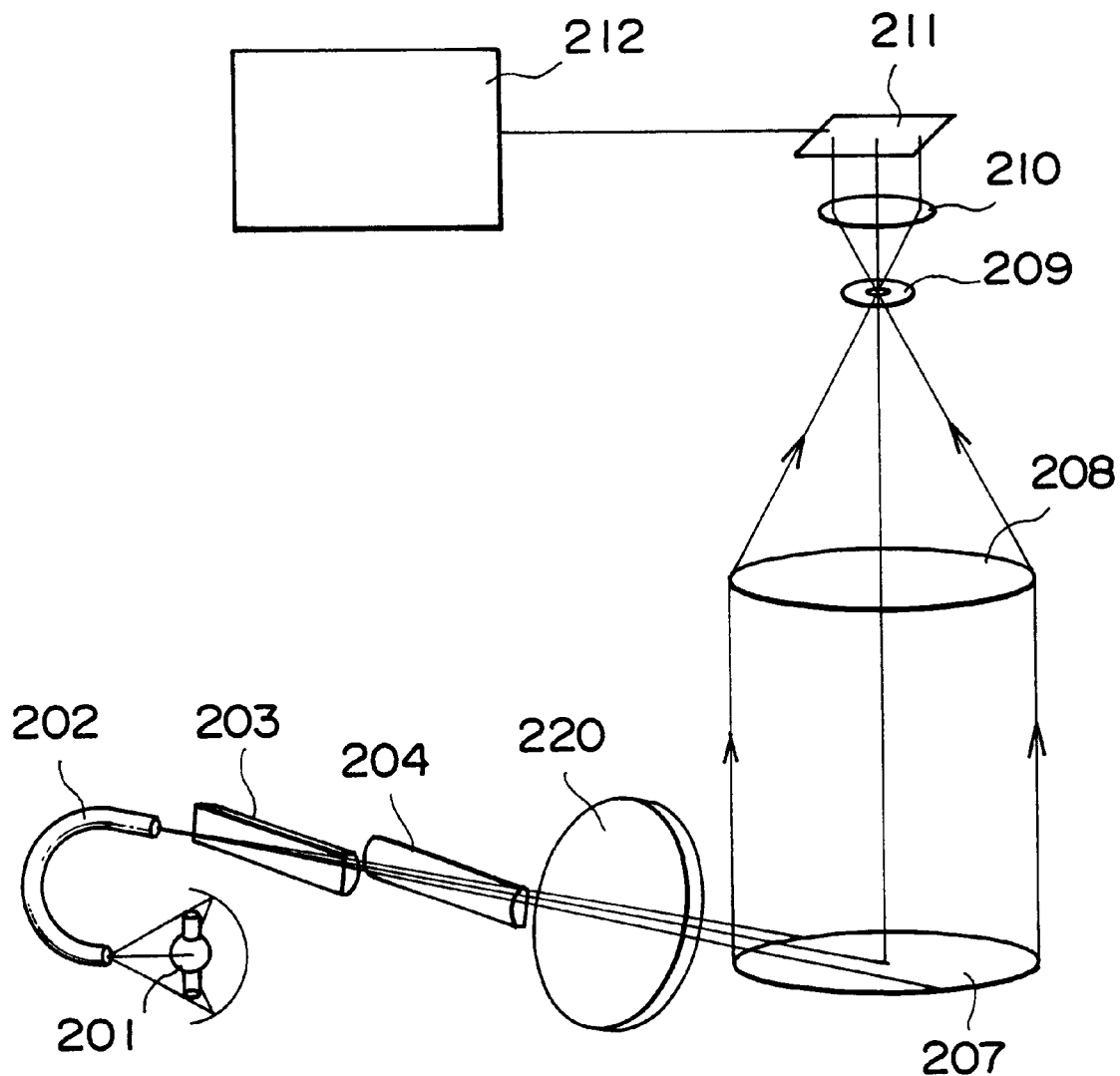
FIG. 8 is a view for showing the structure of a defect testing apparatus according to a variation of the second embodiment.
Figure 9A:
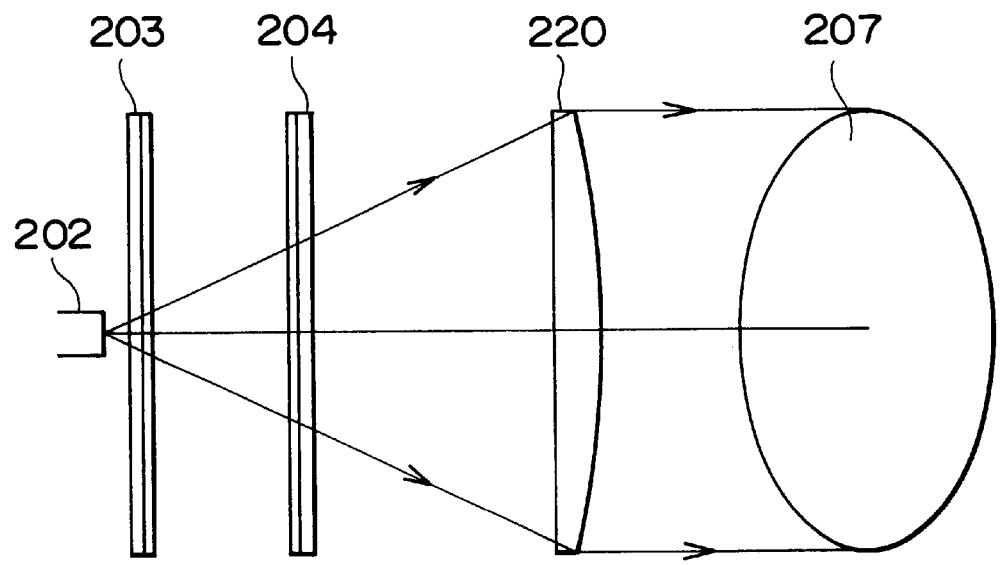
FIGS. 9A and 9B are views for showing the lens structures of an illumination optical system of the defect testing apparatus according to the variation of the second embodiment.
Figure 9B:
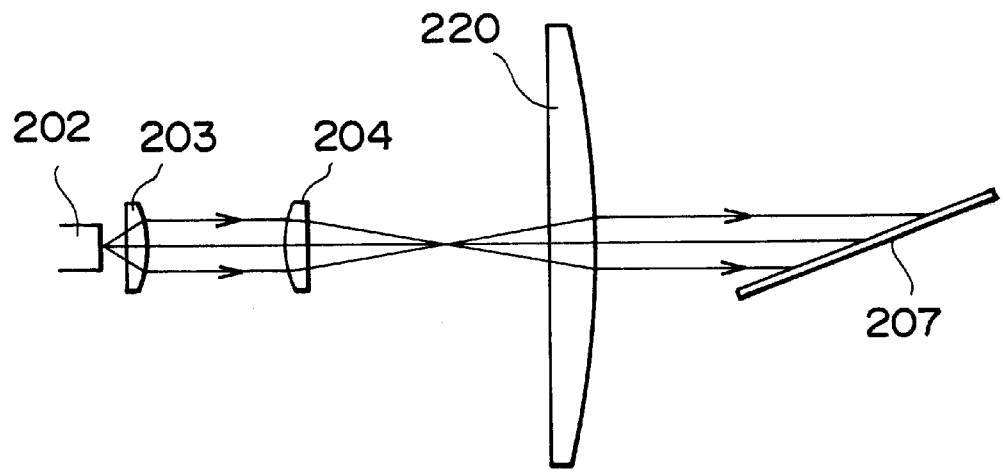

Next, as a variation of the second embodiment, there is shown a case in which the third cylindrical lens and the fourth cylindrical lens are replaced with a single spherical lens 220. FIG. 8 is a perspective view of this variation. FIG. 9A is a top view of an illumination optical system in this variation, while FIG. 9B is a side view thereof. In case of this variation, the focal length $f_3$ of the third cylindrical lens and the focal length $f_0$ of the fourth cylindrical lens are equal to each other, and the distance between the principal plane of the spherical lens 220 and the tested object 207 is equal to the focal length $f_0$ of the fourth cylindrical lens. For this reason, the following condition is added to be satisfied:

$$f_0 = f_3 = e_3$$

Values for this variation will be shown in Table 3.

TABLE 3

| $e_0$ | 22 mm | $f_1$ | 19.6 mm |
|---|---|---|---|
| $e_1$ | 110 mm | $f_2$ | 101.5385 mm |
| $e_2$ | 240 mm | $f_3$ | 360 mm |
| $e_3$ | 360 mm | F | −30 mm |
| Total length | 720 mm | $f_0$ | 360 mm |

Figure 10A:
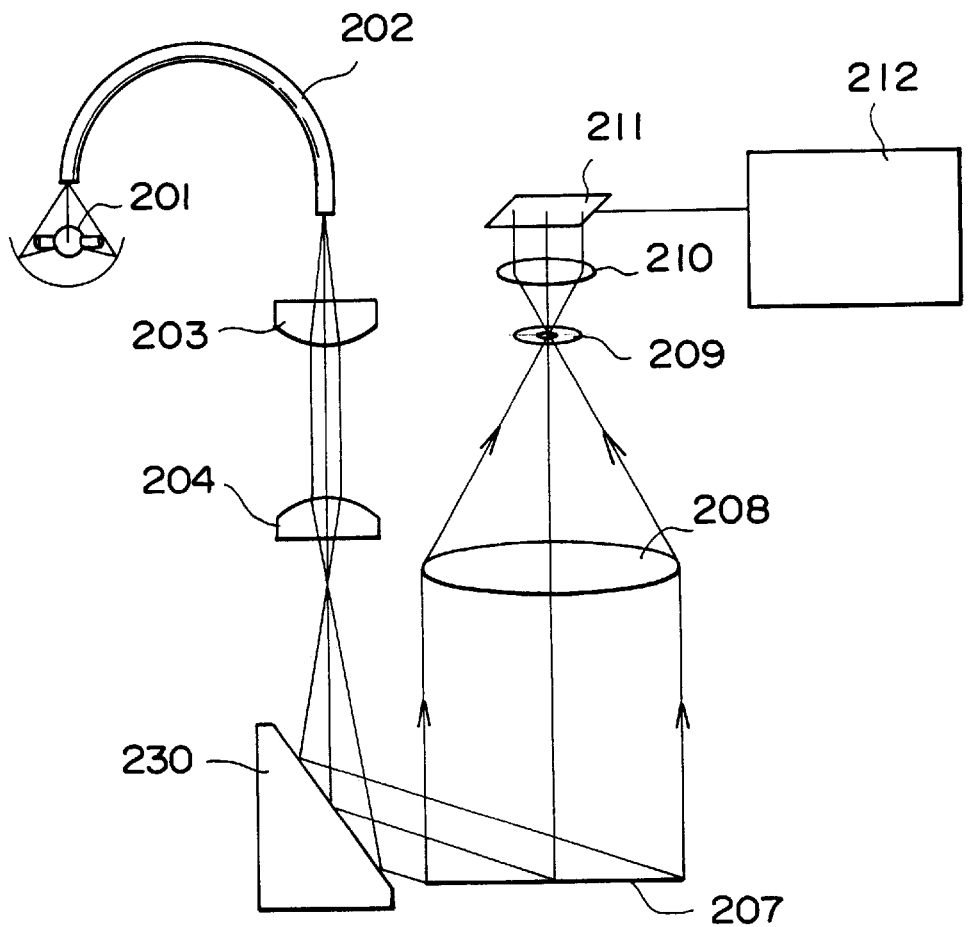
FIGS. 10A and 10B are views for showing the structures of a defect testing apparatus according to another variation of the second embodiment.
Figure 10B:
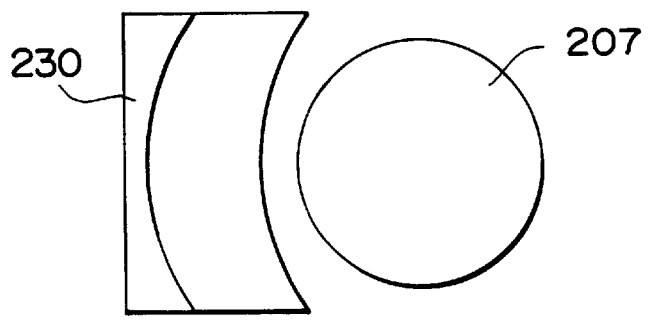

Furthermore, as another variation of the second embodiment, there is shown a case in which, instead of the third cylindrical lens and the fourth cylindrical lens, a reflection mirror 230 is employed. FIG. 10A is a schematic view of this variation, seen from the lateral side thereof. FIG. 10B is a top view of the reflection mirror 230, seen from above the apparatus. In case of the reflection mirror, it is possible to conduct processing comparatively freely by polishing the curved surface of the reflection mirror. For this reason, it is comparatively easy to change the curvature of the curved surface in a perpendicular direction. Since the arrangement can be designed under the condition of $f_0=e_3$, that is, the distance $e_3$ between the principal plane of the reflection mirror 230 and the tested object 207 is equal to the focal lens $f_0$ of the illumination area in the longitudinal direction, the degree of freedom in designing can be enhanced. Values for this variation will be shown in Table 4.

TABLE 4

| $e_0$ | 22.5 mm | $f_1$ | 19.15385 mm |
|---|---|---|---|
| $e_1$ | 207.5 mm | $f_2$ | 276.6667 mm |
| $e_2$ | 130 mm | $f_3$ | 240 mm |
| $e_3$ | 360 mm | F | −30 mm |
| Total length | 720 mm | $f_0$ | 360 mm |

The radius of curvature of a spherical concave mirror can be determined from the fact that it is double the focal length thereof. As a result, it is determined that the radius of curvature of the concave mirror in the longitudinal direction of the illumination light flux is 720 mm, and the radius of curvature of the concave mirror in the latitudinal direction of the illumination light flux is 360 mm. Furthermore, in case of the reflection mirror, the concave surface thereof can be parabolic, instead of spherical, so as to further optimize the reflection mirror. Particularly, a wide range should be illuminated in the longitudinal direction. Thus, in case of the spherical reflection mirror, ambient (peripheral) light fluxes can be excessively bent in the direction of the optical axis under the influence of a spherical aberration thereof. As a result, it becomes difficult to obtain parallel light fluxes. Therefore, even the ambient light fluxes can be made parallel to each other if the reflection surface is made parabolic. Assuming the center of the parabolic surface as the origin and the direction of the optical axis of the parabolic surface as axis z, and the axis x and the axis y as the directions perpendicular thereto, the rotating parabolic surface is expressed as follows:

$$z = a(x^2 + y^2)$$

The focal length of this parabolic surface is 1/(4a). Since the focal length of the illumination light flux in the longitudinal direction is 360 mm from the values shown above (in Tables 3 and 4), a rotating parabolic surface which has a coefficient a for the reflection surface of the illumination in the longitudinal direction of 1/1440 (≈0.00694) is employed. However, since the reflection surface is used, the optical axis may not be formed linearly or a high assembling accuracy is required, compared with that for a lens. Such structure may be constituted by so-called toric lens which has a curved surface not rotation-symmetric not only with the reflection mirror, but also with the optical axis. With the illumination as described above, any plural points on the tested object can be illuminated with illumination lights which are substantially parallel to each other and are incident at angles in a predetermined range. Accordingly, even when such a pattern having a pitch as allowing a diffracted light to enter the light receiving optical system is present on the tested object 207, presence of a foreign substance can be tested by rotating the tested object 207 so as to change the direction in which the diffracted light advances into a direction in which there is no light receiving optical system. By thus receiving a light scattered from a flaw, the flaw attached on the tested object 207 can be easily detected.

On the other hand, however, the intensity of the scattered light produced by a flaw fluctuates depending on the direction of illumination, it is preferable that the holder 213 on which the tested object 207 is mounted is rotated so as to receive the light in directions as many as possible in which the diffracted light from the pattern does not enter the light receiving optical system 208. The arrangement is not limited to this. Instead of the tested object 207, the illumination optical systems 203 to 206 may be rotated to change the direction of illumination. Though the foregoing embodiments employ a lens (refraction optical system) to serve as the light receiving optical system 208, it is needless to say that a reflection mirror (a reflection optical system) may be employed, instead.

Third Embodiment

Next, the third embodiment of the present invention will be described. In this embodiment, an illumination light is applied onto a tested object having a pattern of pitch p at an angle of incidence in a range from θa1 to θa2 so that a scattered light from a foreign substance is received by a light receiving optical system at an angle of light reception of ø1 to Å2. In this case, it is required to satisfy the following expression to prevent a diffracted light from a pattern from entering the light receiving optical system:

$$\frac{p(\sin\theta a2 - \sin\phi)}{n} < \lambda < \frac{p(\sin\theta a1 - \sin\phi 2)}{n-1}$$

where λ is an illuminating wavelength, and n is an integer. When θa1<θa2 and Å1<Å2, the angle of incidence and the angle of light reception are indicated as angle of deviations from the direction of the normal line of the tested object as the direction of 0°. That is, it is possible to satisfy a condition for preventing a diffracted light from the pattern from entering the light receiving optical system by selecting the illuminating wavelength λ in accordance with the pitch p of the pattern.

Figure 11:
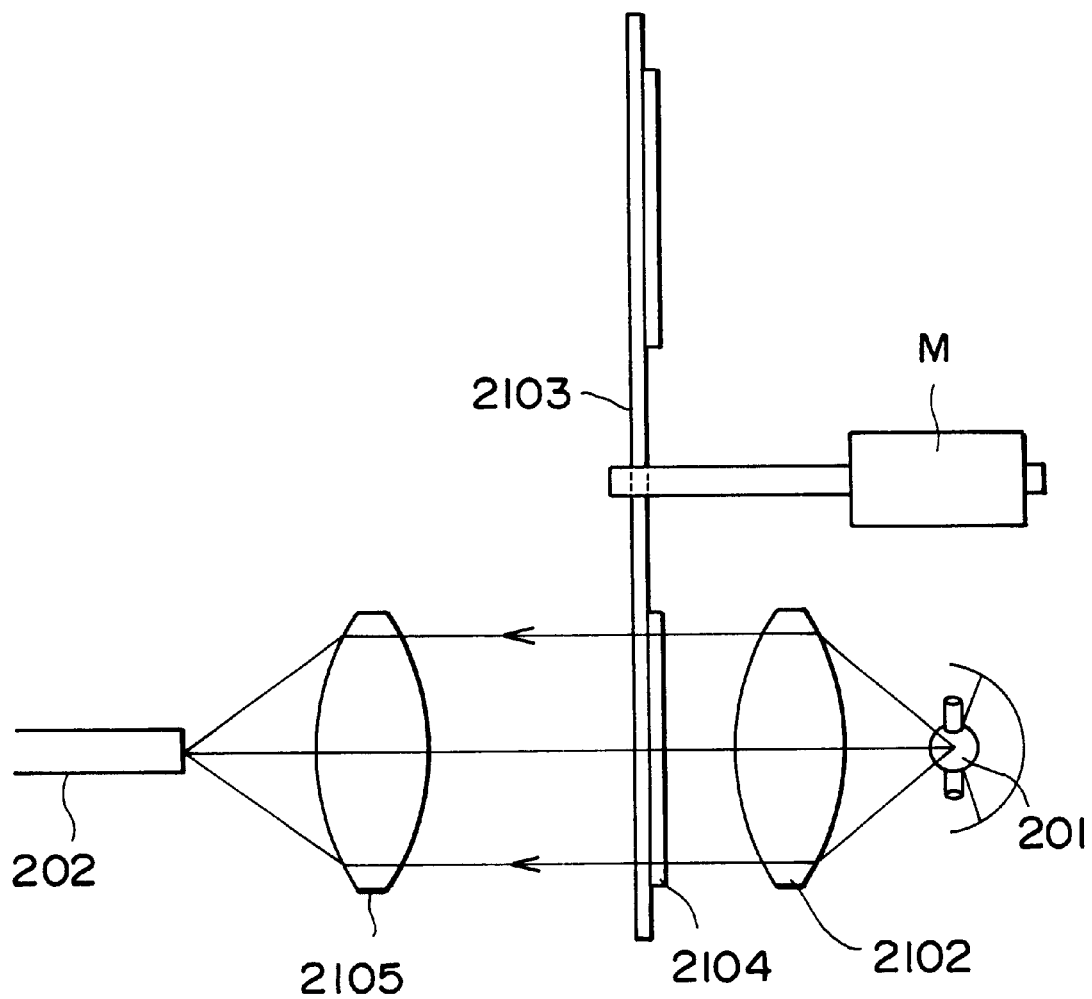
FIG. 11 is a view for showing the structure of a defect testing apparatus, in the vicinity of a light source unit, according to a third embodiment.

FIG. 11 is a view for showing the structure in the vicinity of a light source unit of a defect testing apparatus according to the third embodiment. The third embodiment is different from the second embodiment in that a wavelength switching mechanism is provided in the light source unit in the third embodiment. Other structures are the same as those in the second embodiment so that description thereof will be omitted. A light flux from a light source 201 such as a halogen lamp is introduced into a light guide fiber 202 through a condenser lens 2102, a wavelength limiting filter 2104 mounted on a turret 2103 and an input lens 2105. Then, the illumination light is applied onto a tested object 207 through the illumination optical systems 203 to 206 described above, and a test with a scattered light is conducted in the procedure described above. The turret 2103 is provided with a plurality of filters having different limitation wavelengths. Then, a motor M is driven in accordance with a signal from an unrepresented control system so as to rotating the turret 2103. Thus, it is possible to select a wavelength limiting filter to be inserted into an optical path of a light flux from the light source 201. As the wavelength limiting filter, an interference filter, a color glass filter, or the like, can be used. As described in the foregoing first embodiment, it is possible to prevent the diffracted light from entering the light receiving optical system further effectively by rotating the test stage.

Figure 12:
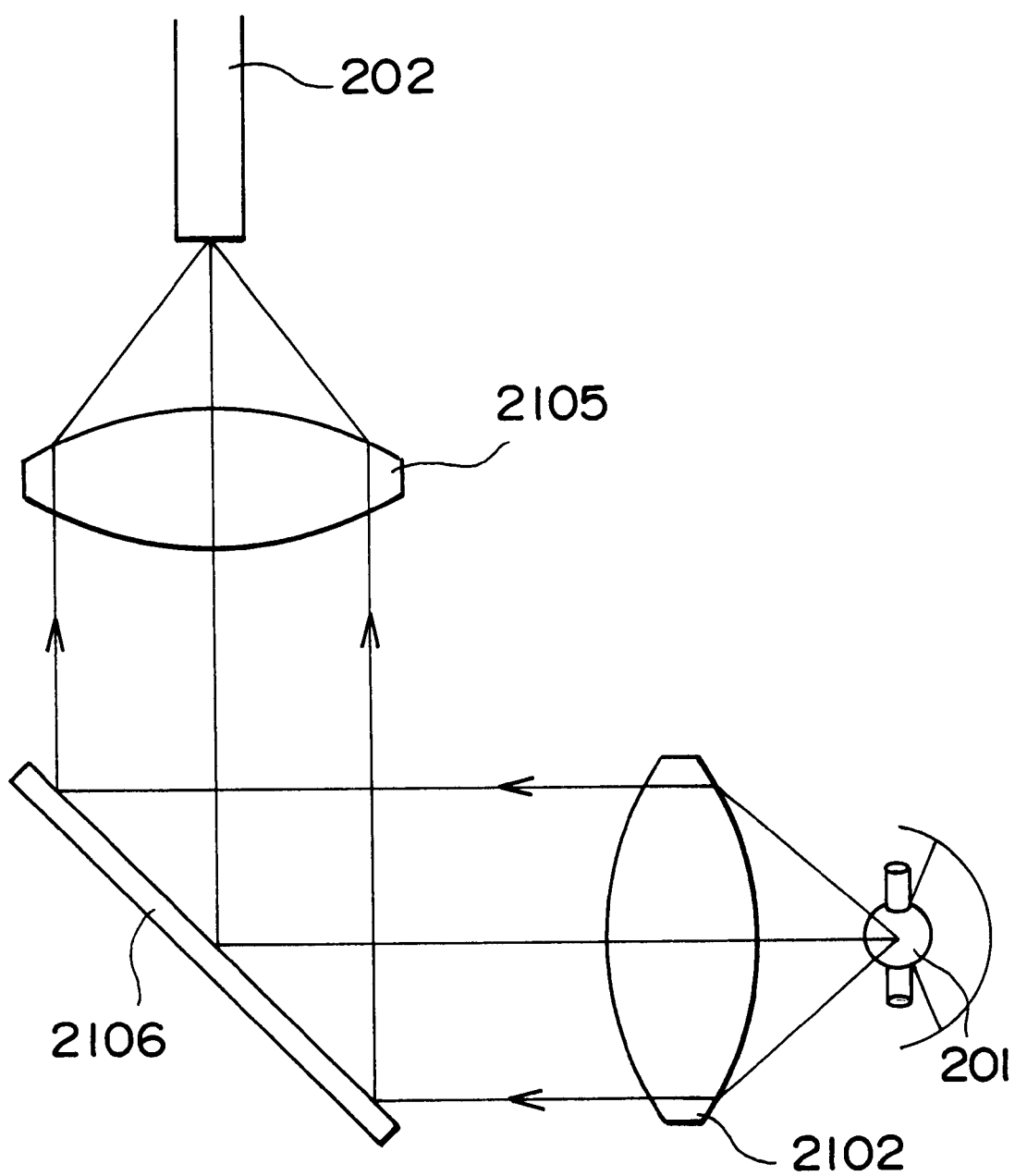
FIG. 12 is a view for showing the structure of a defect testing apparatus, in the vicinity of a light source unit, according to a variation of the third embodiment.

As a variation of the third embodiment, if it is arranged to select a wavelength in the light source unit, the wavelength may be selected by using a spectroscopic device 2106, such as a diffraction grating or a prism, as shown in FIG. 12.

Next, another variation of the third embodiment will be described. The tested object 207 having the pattern of pitch p can be considered as a diffraction grating. For this reason, in accordance with the wavelength λ of the illumination light, the diffraction angle Øn of the diffracted light of the n-th order can be expressed as follows:

sin Øn=sin θ−nλ/p, where θ is the angle of incidence of the illumination light.

Figure 13:
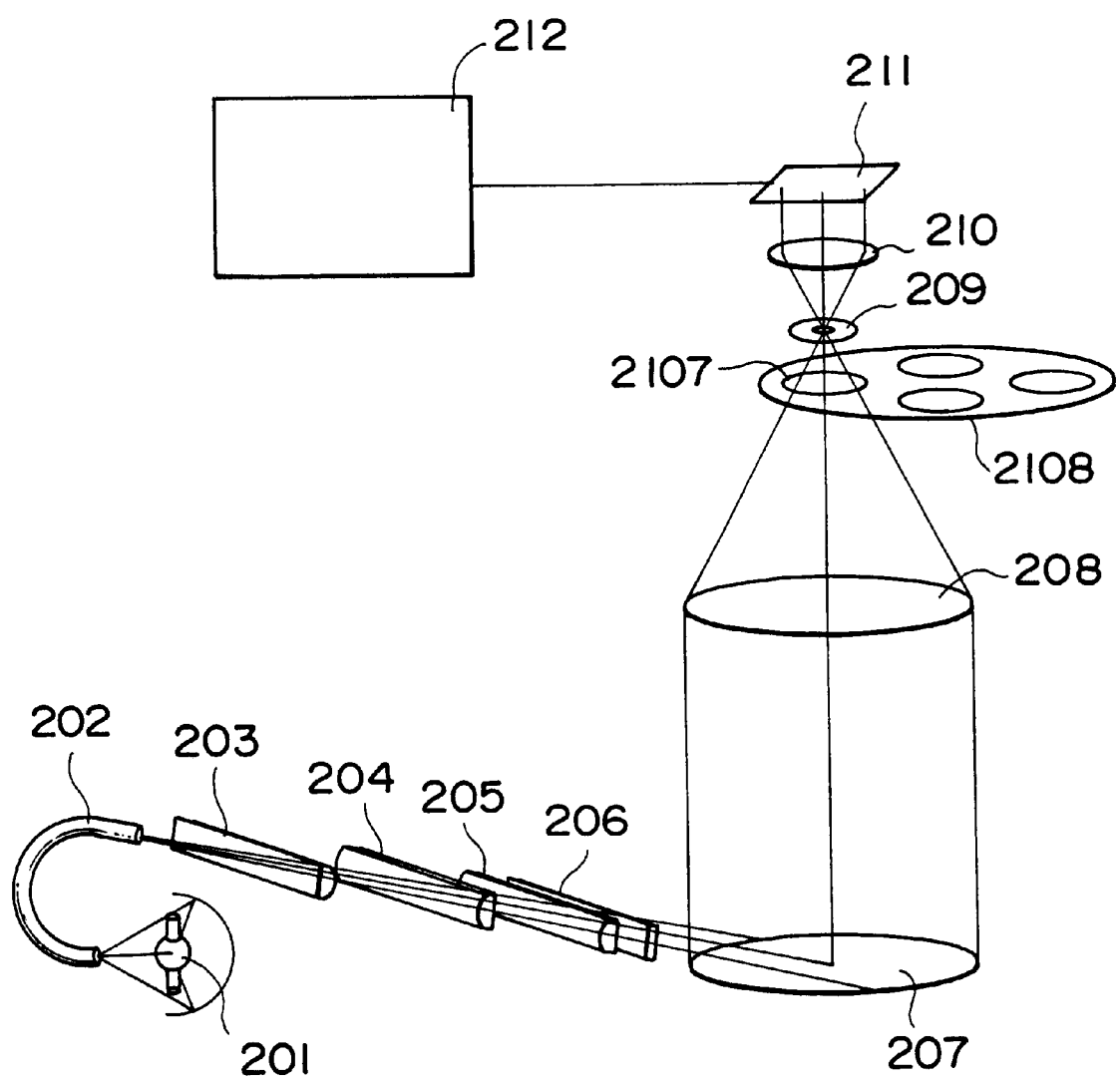
FIG. 13 is a view for showing the structure of a defect testing apparatus according to another variation of the third embodiment.

When the angle of light reception of the light receiving optical system 208 coincides with the angle of diffraction of the pattern, a filter 2107 which does not transmit a light with the corresponding wavelength is inserted into the optical path, as shown in FIG. 13. Then, the test stage is rotated. Thus, the diffracted light from the pattern does not enter the image pick-up device 211. On the other hand, a scattered light from a foreign substance or a flaw spreads substantially equi-directionally so that the scattered light passing through the filter enters the light receiving optical system 208 to be detected by the image pick-up device 211. The filter 2107 is attached to the turret 2108 which is rotatable in the same manner as that shown in FIG. 12, and is arranged to be selected whenever needed in the same manner as that described above.

The present invention is not limited to the foregoing embodiments. An actual circuit pattern which is formed on a substrate such as a wafer has a complicated form so that circuit devices are not necessarily arranged at a uniform pitch on the entire surface of the substrate. As a result, it is possible to prevent an unnecessary diffracted light from entering the image pick-up device more effectively by using such an illumination optical system as capable of telecentric flat illumination, as described in the second embodiment, and the wavelength selecting filter described in the third embodiment in a combined manner.

An amount of rotation of the tested object in the second embodiment and an illumination wavelength band range in the third embodiment are determined in advance so that the diffracted light does not enter the light receiving optical system. However, the present invention is not limited to such cases. When a periodic signal which is corresponding to the period of repetition of an exposure pattern is present in the image of the scattered light of the tested object which is obtained by the image pick-up device, the tested object may be rotated by the unrepresented control system as described above so as to reduce the illumination wavelength band range, thereby automatically finding out a condition for preventing the diffracted light from the pattern from entering the light receiving optical system.

Furthermore, it may be arranged such that the tested object is rotated to allow the diffracted light from the pattern to enter the light receiving optical system, the pattern on the tested object is tested, as disclosed by the present applicants in the Japanese Patent Laid-Open Application No. 11-51874, and the direction of illumination and the direction of the pattern on the tested object are changed so as to prevent the diffracted light from entering the light optical system, thereby testing a foreign substance and a flaw.

As described above, according to the defect testing apparatus of the present invention, it is possible to prevent a diffracted light from a pattern from entering the light receiving optical system by properly rotating the wafer in accordance with the relation between the spread angle of the illumination light flux and the direction of arrangement of patterns on the wafer. As a result a defect test with efficiency and reliability can be attained.

Also according to the present invention, it is possible to reduce a range for angles of illumination lights for illuminating any plural points on a tested object. Since the illumination lights are substantially equal to each other, it is possible to make the illumination conditions uniform on any point on the tested object. Then, by rotating the tested object and the illumination light relatively with each other, it is possible to prevent a harmful (unnecessary) diffracted light coming from a pattern on the tested object from entering the light receiving optical system when scattered light is received. In this manner, it is possible to detect a foreign substance, or the like, on the tested object at high speed with accuracy and with high sensitivity.

Furthermore, according to the present invention, it is possible to select an illumination wavelength condition for preventing the diffracted light from the pattern from entering the light receiving optical system. Then, it is possible to detect a scattered light from a foreign substance or a flaw on the tested object more effectively with high sensitivity by rotating the tested object and the illumination light relatively with each other.

What is claimed is:

1. A defect testing apparatus, comprising:

a light source;

an illumination optical system which applies a light flux from the light source onto a tested substrate having a repeated pattern at a predetermined angle of incidence;

a light receiving optical system which receives a scattered light from the tested substrate;

an image pick-up device which picks up an image formed by the light receiving optical system;

a display device which displays the image obtained by the image pick-up device; and a test stage which mounts the tested substrate thereon at the time of testing, wherein the tested substrate and the illumination optical system are rotatable relatively to each other so that a diffracted light from the tested substrate is diffracted in a direction other than that of the light receiving optical system.

2. The defect testing apparatus according to claim 1, wherein the test stage is rotatable around the axis in the normal direction of the tested substrate.

3. The defect testing apparatus according to claim 1, wherein the light receiving optical system is telecentric on the object side.

4. The defect testing apparatus according to claim 1, further comprising an image processing apparatus which conducts an image processing in accordance with information obtained by the image pick-up device so as to detect a defect.

5. The defect testing apparatus according to claim 1, wherein said illumination optical system comprises at least two optical devices each having a refracting power only in a plane formed by an optical axis of said illumination optical axis and an optical axis of said light receiving optical system, and an optical device having a refracting power in a plane which is perpendicular to the plane formed by the optical axis of said illumination optical system and the optical axis of said light receiving optical system.

6. The defect testing apparatus according to claim 5, further comprising a wavelength selecting device which selects a light with a specific wavelength on the illumination optical system side, rather than the image pick-up device side.

7. The defect testing apparatus according to claim 1, further comprising a wavelength selecting device which selects a light with a specific wavelength on the illumination optical system side, rather than the image pick-up device side.

8. A defect testing apparatus, comprising:

a light source;

an illumination optical system which applies a light flux from the light source onto a tested substrate having a repeated pattern at a predetermined angle of incidence;

a light receiving optical system which receives a scattered light from the tested substrate;

an image pick-up device which picks up an image formed by the light receiving optical system;

a display device which displays the image obtained by the image pick-up device; and a test stage which mounts the tested substrate thereon at the time of testing, wherein the tested substrate and the illumination optical system are arranged to be rotatable relatively to each other, wherein the light receiving optical system is telecentric on the object side, and wherein, when the light flux is applied on the tested substrate with a spread angle on a flat surface which is perpendicular to the entrance surface of the illumination optical system and contains an optical axis thereof, the test stage or the illumination optical system is rotated to make an angle of rotation between the optical axis of the illumination optical system and the direction of arrangement of the repeated pattern to be more than or equal to ½ of the spread angle.

9. The defect testing apparatus according to claim 8, further comprising a light flux shaping member which makes the spread angle variable.

10. The defect testing apparatus according to claim 9, further comprising a calculation device which determines the spread angle and an angle of rotation of the tested substrate or the illumination optical system in accordance with information on the pattern on the tested substrate.

11. A defect testing apparatus, comprising:

a light source;

an illumination optical system which applies a light flux from the light source onto a tested substrate having a repeated pattern at a predetermined angle of incidence;

a light receiving optical system which receives a scattered light from the tested substrate;

an image pick-up device which picks up an image formed by the light receiving optical system;

a display device which displays the image obtained by the image pick-up device; and a test stage which mounts the tested substrate thereon at the time of testing, wherein the tested substrate and the illumination optical system are arranged to be rotatable relatively to each other, wherein the light receiving optical system is telecentric on the object side, and wherein, when the light flux is applied on the tested substrate with a spread angle on a flat surface which is perpendicular to the entrance surface of the illumination optical system and contains an optical axis thereof and when the repeated pattern has two directions of arrangement, the test stage or the illumination optical system is rotated to make an angle of rotation between the optical axis of the illumination optical system and either one of the two directions of arrangement to be more than or equal to ½ of the spread angle with reference to the angle θ1 which satisfies the following conditions (1) to (4):

$$\tan \theta 1 = mypx/mxpy \qquad (1);$$

$$-px/\lambda \leq mx \leq 0 \qquad (2);$$

$$-py/\lambda \leq my \leq 0 \qquad (3);$$

and $$(mx\lambda/px)^2 + (my\lambda/py)^2 = 1 \qquad (4),$$

where px is the pitch of one of the directions of arrangement, py is the pitch of the other of the directions of arrangement, mx is the order of diffraction of diffracted light from the tested substrate with respect to the former direction, my is the order of diffraction of diffracted light from the tested substrate with respect to the latter direction, and λ is the wavelength of the light flux.

12. A defect testing method, comprising:

an illumination step which applies a light flux onto a tested substrate having a repeated pattern at a predetermined angle of incidence by an illumination optical system;

a light receiving step which receives a scattered light from the tested substrate;

an image pick-up step which picks up an image formed by the light receiving step; and a rotation step which rotates the tested substrate and the illumination optical system relatively to each other so that diffracted light from the tested substrate is diffracted in a direction other than that in which the scattered light from the tested substrate is received in the light receiving step.

13. A defect testing method, comprising:

an illumination step which applies a light flux onto a tested substrate having a repeated pattern at a predetermined angle of incidence by an illumination optical system;

a light receiving step which receives a scattered light from the tested substrate;

an image pick-up step which picks up an image formed by the light receiving step;

a rotation step which rotates the tested substrate and the illumination optical system relatively to each other;

a first image processing step which conducts an image processing to the image by the scattered light from the tested substrate illuminated at a predetermined direction;

a second image processing step which rotates the tested substrate and the illumination optical system relatively to each other at 360/n (n:integer) degree from the predetermined direction, and conducts an image processing to a picked-up image;

an image processing repeating step which repeats the second image processing step n–1 times; and a third image processing step which further conducts an image processing to an image processing result from the first image processing step and to image processing results from the image processing repeating step.

14. A defect testing method, comprising:

an illumination step which applies a light flux onto a tested substrate having a repeated pattern at a predetermined angle of incidence by an illumination optical system;

a light receiving step which receives a scattered light from the tested substrate;

an image pick-up step which picks up an image formed by the light receiving step;

a rotation step which rotates the tested substrate and the illumination optical system relatively to each other;

a first image pick-up step which picks-up an image by the scattered light from the tested substrate illuminated at a predetermined direction;

a second image pick-up step which rotates the tested substrate and the illumination optical system relatively to each other at 360/n (n:integer) degree from the predetermined direction, and picks up an image;

an image pick-up repeating step which repeats the second image image-pick step n–1 time; and an image processing step which synthesizes the picked-up image by the first image pick-up step and the picked-up images by the image pick-up repeating step, and conducts an image processing to the synthesized image.

* * * * *